(12) United States Patent
Aoki et al.

(10) Patent No.: US 12,111,431 B2
(45) Date of Patent: Oct. 8, 2024

(54) RADIATION DETECTOR AND RADIATION IMAGING DEVICE INCLUDING SAME

(71) Applicants: NATIONAL UNIVERSITY CORPORATION SHIZUOKA UNIVERSITY, Shizuoka (JP); ANSeeN Inc., Shizuoka (JP)

(72) Inventors: Toru Aoki, Hamamatsu (JP); Katsuyuki Takagi, Hamamatsu (JP); Kosuke Kimura, Hamamatsu (JP); Akifumi Koike, Hamamatsu (JP)

(73) Assignees: NATIONAL UNIVERSITY CORPORATION SHIZUOKA UNIVERSITY (JP); ANSEEN INC. (JP)

( * ) Notice: Subject to any disclaimer, the term of this patent is extended or adjusted under 35 U.S.C. 154(b) by 0 days.

(21) Appl. No.: 17/793,292

(22) PCT Filed: Nov. 24, 2020

(86) PCT No.: PCT/JP2020/043669
§ 371 (c)(1),
(2) Date: Jul. 15, 2022

(87) PCT Pub. No.: WO2022/113170
PCT Pub. Date: Jun. 2, 2022

(65) Prior Publication Data
US 2023/0341571 A1    Oct. 26, 2023

(51) Int. Cl.
*G01T 1/36* (2006.01)
*A61B 6/03* (2006.01)
*A61B 6/42* (2024.01)

(52) U.S. Cl.
CPC .............. *G01T 1/365* (2013.01); *A61B 6/035* (2013.01); *A61B 6/4241* (2013.01)

(58) Field of Classification Search
CPC ........ G01T 1/365; A61B 6/035; A61B 6/4241
See application file for complete search history.

(56) References Cited

U.S. PATENT DOCUMENTS

| | | | |
|---|---|---|---|
| 2008/0099689 A1 | 5/2008 | Nygard et al. | 250/370.09 |
| 2013/0105701 A1* | 5/2013 | Han | G01T 1/366 250/336.1 |
| 2019/0213759 A1 | 7/2019 | Lee et al. | |

FOREIGN PATENT DOCUMENTS

| | | |
|---|---|---|
| JP | H 11-128214 A | 5/1999 |
| JP | 2013-096993 A | 5/2013 |

(Continued)

OTHER PUBLICATIONS

English translation of the International Preliminary Report on Patentability (IPRP) (Chapter 1 or II of the PCT Treaty) mailed Jun. 8, 2023 with a Notification from the International Bureau (Form PCT/IB/338) in corresponding PCT International Application No. PCT/JP2020/043669.

(Continued)

*Primary Examiner* — Hugh Maupin
(74) *Attorney, Agent, or Firm* — OSTROLENK FABER LLP

(57) ABSTRACT

An object is to provide intensity information and energy information while reducing processing load and power consumption. In a radiation detector, a radiation detection element, in which a plurality of pixels each configured to generate an electric charge corresponding to energy of X-rays penetrating a subject is two-dimensionally arranged, and a plurality of read circuits each configured to output an intensity signal of transmitted X-rays based on the electric charge generated by each of the plurality of pixels are stacked with each other, and some read circuits thinned out from a plurality of read circuits each generate a spectral (Continued)

signal related to a spectrum of a transmitted X-ray based on the electric charge and output the spectral signal.

7 Claims, 7 Drawing Sheets

(56) References Cited

FOREIGN PATENT DOCUMENTS

| | | |
|---|---|---|
| JP | 2014-045896 A | 3/2014 |
| JP | 2015-104664 A | 6/2015 |
| JP | 6204992 B2 | 9/2017 |
| JP | 2017-529204 A | 10/2017 |
| JP | 2020-099667 A | 7/2020 |
| TW | 202011046 A | 3/2020 |
| WO | WO 2015/076067 A1 | 5/2015 |
| WO | WO 2016/029845 A1 | 3/2016 |

OTHER PUBLICATIONS

International Search Report mailed Jan. 19, 2021 in corresponding PCT International Application No. PCT/JP2020/043669.
Written Opinion mailed Jan. 19, 2021 in corresponding PCT International Application No. PCT/JP2020/043669.
Office Action dated Oct. 5, 2022 in counterpart Taiwanese Patent Application No. 110139310.
Extended European Search Report dated Aug. 23, 2023, issued in corresponding European Patent Application No. 20963435.1.

* cited by examiner

RADIATION DETECTOR AND RADIATION IMAGING DEVICE INCLUDING SAME

CROSS-REFERENCE TO RELATED APPLICATION

The present application is a 35 U.S.C. § 371 national stage application of International Application No. PCT/JP2020/043669, filed Nov. 24, 2020, the disclosure of which is incorporated herein by reference. The PCT International Application was published in the Japanese language.

TECHNICAL FIELD

The present disclosure describes a radiation detector and a radiation imaging device including same.

BACKGROUND ART

As a conventional imaging device using X-rays, an X-ray CT (Computed Tomography) apparatus has been known as described in Patent Literature 1 below. This X-ray CT apparatus has a function of reconstructing a CT image capable of discriminating a substance by detecting X-rays penetrating a subject at two or more energy levels (hereinafter referred to as spectral CT). According to the spectral CT, it is possible to obtain not only a CT image, which is a distribution of linear attenuation coefficients, but also a distribution of physical property data such as effective atomic numbers.

CITATION LIST

Patent Literature

Patent Literature 1: Japanese Unexamined Patent Publication No. 2020-99667

SUMMARY OF INVENTION

Technical Problem

The imaging device having the above-mentioned spectral CT function may generate a cross-sectional image obtained by superimposing a distribution of physical property data, which is mapped to a color, on a normal CT image. In such an imaging device, when a configuration including a radiation detector having a plurality of pixels is adopted, it is necessary to acquire intensity information used to reconstruct a CT image and intensity information of two or more energy levels (hereinafter referred to as "energy information") from all the pixels. As a result, in the conventional imaging device, processing load and power consumption tend to increase.

The disclosure describes a radiation detector and a radiation imaging device including the same capable of providing intensity information and energy information while reducing processing load and power consumption.

Solution to Problem

A radiation detector which is an aspect of the disclosure comprises an electric charge generation unit which includes a plurality of electric charge generation regions each configured to generate an electric charge corresponding to energy or the number of particles of radiation penetrating a subject, and a plurality of read circuits which are stacked with the electric charge generation unit. The plurality of electric charge generation regions are two-dimensionally arranged in the electric charge generation unit, the plurality of read circuits each configured to output an intensity signal of the radiation based on the electric charge generated by each of the plurality of electric charge generation regions, and some read circuits thinned out from the plurality of read circuits each generate a spectral signal related to a spectrum of the radiation based on the electric charge and output the spectral signal.

In this radiation detector, an electric charge corresponding to energy or the number of particles of incident radiation is generated in each of the plurality of electric charge generation regions of the electric charge generation unit, and intensity information of radiation based on the electric charge is output in a read circuit corresponding to each of the electric charge generation regions. In addition, a spectral signal related to a spectrum of the radiation based on the electric charge is generated and output in each of some read circuits thinned out from the plurality of read circuits. In this way, it is possible to reduce energy information for each electric charge generation region output by the radiation detector while maintaining resolution of intensity information of an image of the subject, and as a result, it is possible to reduce processing load and power consumption while maintaining the resolution of the image of the subject to be output.

In the aspect, the some read circuits may each generate the spectral signal based on the electric charge generated in each of the electric charge generation regions disposed to correspond to the read circuits. In this case, based on the electric charge generated in each of some electric charge generation regions thinned out from the plurality of electric charge generation regions, a spectral signal related to a spectrum of radiation incident on each of the electric charge generation regions is generated and output. In this way, it is possible to output intensity information and energy information while reducing processing load and power consumption.

In the aspect, the some read circuits may each generate the spectral signal based on the electric charge generated in each of the corresponding electric charge generation regions disposed to correspond to the read circuits and the electric charge generated in the electric charge generation regions within a predetermined range of each of the corresponding electric charge generation regions. In this case, based on an electric charge generated in a plurality of electric charge generation regions included in a predetermined range among a plurality of electric charge generation regions, a spectral signal obtained by integrating spectra of radiation incident on the respective electric charge generation regions in the predetermined range is generated and output. In this way, it is possible to output intensity information and energy information while reducing processing load and power consumption.

In the aspect, the some read circuits may each generate, as the spectral signal, data indicating a plurality of combinations of energy of the radiation and an intensity value corresponding to the energy. According to this configuration, it is possible to efficiently output energy information for obtaining a distribution of physical property data from only the some read circuits thinned out. As a result, it is possible to output intensity information and energy information while reducing processing load and power consumption.

A radiation imaging device according to another aspect of the disclosure includes the radiation detector, and a processor configured to generate an image based on the intensity signal and the spectral signal output from the radiation detector. According to this radiation imaging device, it is possible to realize generation of an image based on intensity information and energy information while reducing processing load and power consumption.

In another aspect, the processor may generate information representing an image of the subject as high-resolution luminance information based on the intensity signal output from each of the plurality of read circuits, generate information representing a distribution of physical properties of the subject as low-resolution color information based on the spectral signal output from each of the some read circuits, and generate a color image of the subject by combining the luminance information and the color information. According to this configuration, a delicate image of the subject may be efficiently generated in a state where a physical property distribution may be visually recognized.

In another aspect, the processor may have a function of reconstructing a CT image based on the intensity signal and the spectral signal output from the radiation detector. In such a configuration, spectral CT with reduced processing load and power consumption may be realized.

Advantageous Effects of Invention

A radiation detector and a radiation imaging device of the disclosure may provide intensity information and energy information while reducing processing load and power consumption.

DESCRIPTION OF EMBODIMENTS

Hereinafter, a radiation detector and a radiation imaging device of the disclosure will be described in detail with reference to the accompanying drawings. In the description of the drawings, the same elements are designated by the same reference symbols, and duplicate description is omitted.

Figure 1:
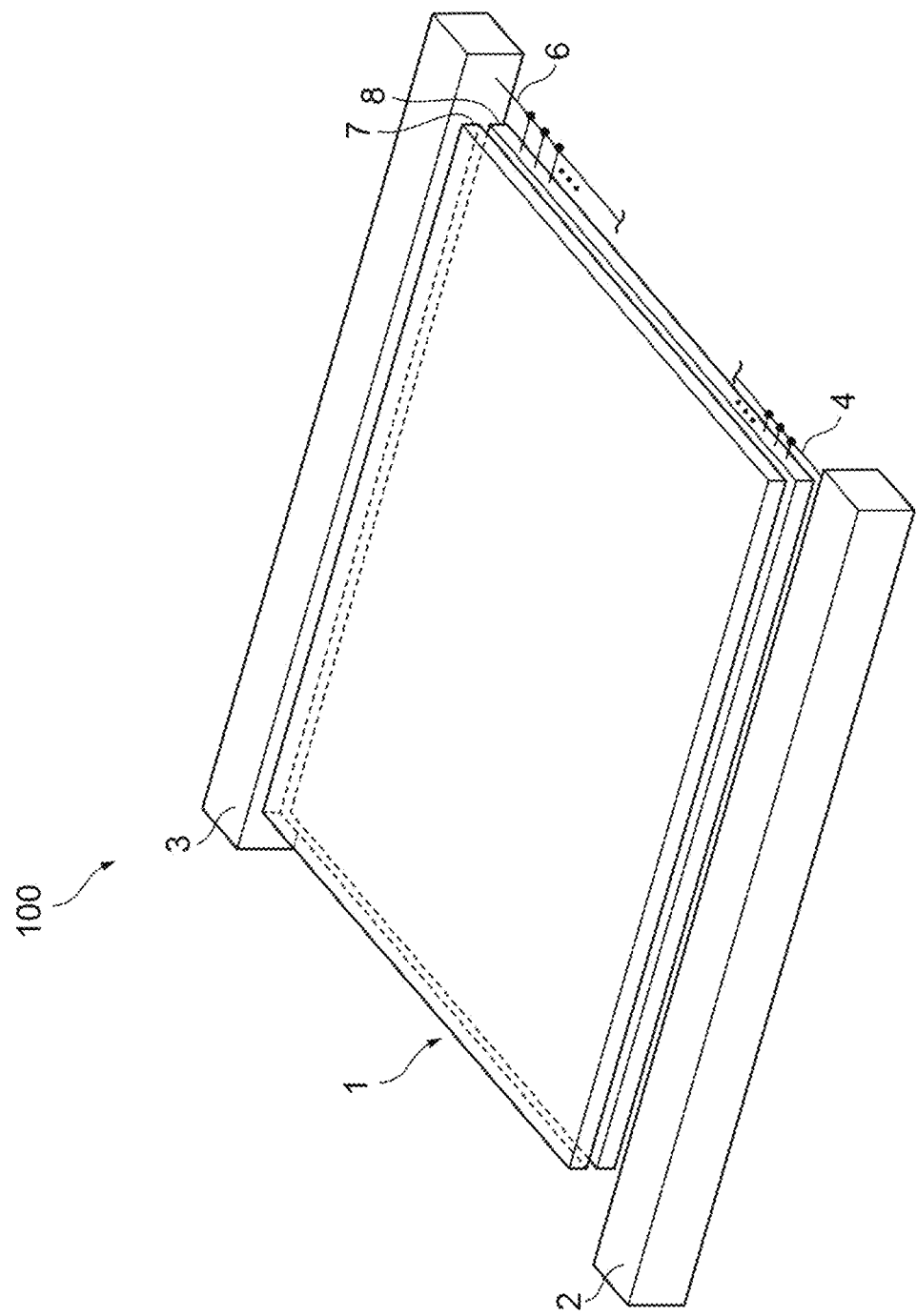
FIG. 1 is a perspective view illustrating a radiation detector 100 according to an embodiment.

A radiation detector 100 according to an embodiment illustrated in FIG. 1 is a device for obtaining a cross-sectional image based on radiation that reaches through a subject. The radiation may be, for example, gamma rays, X-rays, alpha rays, beta rays, etc., and is X-rays in the present embodiment. The radiation detector 100 includes a radiation detection element 1, a processing unit 2, and a controller 3.

The radiation detection element 1 has a rectangular plate-shaped read circuit board 8 and a rectangular plate-shaped detection element board (electric charge generation unit) 7 stacked on the read circuit board 8. The detection element board 7 is a substrate made of a material that generates an electric charge corresponding to energy of an X-ray that enters by penetrating the subject. However, when a particle beam is detected as radiation, the detection element board 7 is made of a material that generates an electric charge corresponding to the number of particles of radiation. The detection element board 7 has a plurality of pixels, and generates electron-hole pairs (electric charge pairs) by X-rays incident on the respective pixels. As the detection element board 7, for example, it is possible to use a Cd (Zn) Te electric charge generator, a Si electric charge generator, a Ge electric charge generator, a GaAs electric charge generator, a GaN electric charge generator, a TlBr electric charge generator, etc. Further, as the detection element board 7, it is possible to use a device including a scintillator and a photodetector for each pixel. The scintillator converts an X-ray into light. The photodetector converts light generated by the scintillator into an electric charge. The read circuit board 8 is a board incorporating a circuit group that generates and outputs a signal based on an electric charge generated for each pixel by the detection element board 7.

Figure 2:
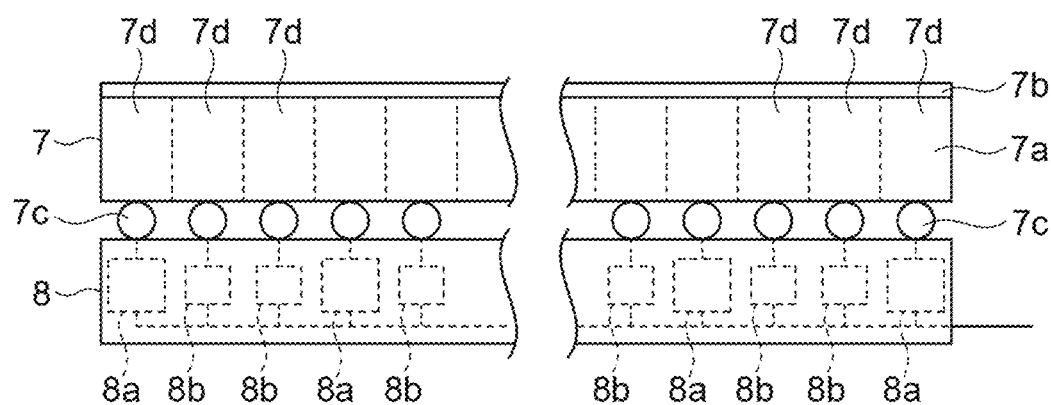
FIG. 2 is a cross-sectional view of a radiation detection element 1 of FIG. 1.

FIG. 2 is a cross-sectional view of the radiation detection element 1. As described above, the detection element board 7 includes a detection element 7a made of a compound semiconductor such as a rectangular flat plate-shaped CdTe, a surface electrode 7b, and a plurality of bump electrodes 7c. The surface electrode 7b is formed on the entire surface of the detection element 7a on a radiation incident side. The bump electrodes 7c, which are two-dimensionally arranged protrusion-shaped electrodes, are formed on a back surface of the detection element 7a. In the detection element board 7 having such a structure, each of a plurality of regions of the detection element 7a facing the bump electrodes 7c forms each of pixels (electric charge generation regions) 7d. When the radiation detector 100 is used, a positive bias voltage is applied to the surface electrode 7b from the outside. As a result, an electric charge corresponding to energy of an X-ray incident on each pixel 7d of the detection element 7a is generated as a current signal, and the current signal is taken out from the corresponding bump electrode 7c to the read circuit board 8. For example, 96×96 bump electrodes 7c are two-dimensionally arranged on the back surface of the detection element 7a. In such a configuration, the radiation detection element 1 has 96×96 pixels 7d arranged two-dimensionally.

The read circuit board 8 is arranged on a back surface side of the detection element board 7 in a state of being bonded to the bump electrodes 7c. The read circuit board 8 incorporates a plurality of read circuits 8a and 8b disposed at positions facing the plurality of pixels 7d of the detection element board 7. The plurality of read circuits 8a and 8b is electrically connected to the plurality of pixels 7d of the detection element board 7 via the bump electrodes 7c, respectively. The plurality of read circuits 8a and 8b is provided at positions facing the plurality of pixels 7d, the read circuits 8a are provided at positions facing pixels 7d obtained by thinning out to one every three pixels from the plurality of pixels 7d in each of two-dimensional array directions, and the read circuits 8b are provided at positions facing pixels 7d other than the thinned-out pixels 7d. That is, the read circuits 8a mean some read circuits thinned out from the plurality of read circuits 8a and 8b facing all the pixels 7d of the detection element board 7. In the present embodiment, the read circuits 8a are provided for every three pixels 7d thinned out. However, a degree of thinning out may be appropriately changed to every eight pixels, every 16 pixels, every 32 pixels, etc.

Each of the read circuits 8b processes an electric charge generated by each pixel 7d of the detection element board 7. Specifically, based on a current signal output by a pixel 7d facing a read circuit 8b, the read circuit 8b stores the current signal for a certain period of time and generates an X-ray intensity signal. Then, the read circuit 8b outputs the intensity signal for each pixel 7d to the processing unit 2 described later. The intensity signal for each pixel 7d output by the read circuit 8b is a signal indicating the intensity of an X-ray incident on each pixel 7d.

The read circuit 8a processes an electric charge generated by the pixel 7d thinned out from all the pixels 7d of the detection element board 7. That is, the read circuit 8a includes a multi-channel analyzer (MCA), counts current signals output by the pixel 7d corresponding to the read circuit 8a as pulse signals, detects heights of the pulse signals as energy of an X-ray photon, and records a count value (intensity value) for each piece of energy. Then, the read circuit 8a generates data indicating a plurality of combinations of a value of energy of an X-ray photon and a count value (intensity value) of the energy as a spectral signal representing a spectrum of an incident X-ray. Then, the read circuit 8a outputs the spectral signal for each pixel 7d to the processing unit 2, which will be described later. Here, the read circuit 8a may have a function of generating and outputting an intensity signal for each pixel 7d in the same manner as the read circuit 8b, in addition to the spectral signal for each pixel 7d corresponding to the read circuit 8a. Since the read circuit 8a has a function of generating a spectral signal, a circuit scale thereof occupied in the read circuit board 8 is larger than that of the read circuit 8b.

Returning to FIG. 1, the processing unit 2 is connected to each of the read circuits 8a and 8b of the read circuit board 8 via a wiring portion 4. The processing unit 2 receives an intensity signal and a spectral signal for each pixel from each of the read circuits 8a and 8b. For example, the processing unit 2 sequentially receives an intensity signal for each pixel from the read circuit 8b, receives a spectral signal for each pixel thinned out from the read circuit 8a, and outputs the received intensity signal and spectral signal for each pixel to the outside.

The controller 3 is connected to each of the read circuits 8a and 8b of the read circuit board 8 via the wiring portion 6. The controller 3 provides the plurality of read circuits 8a and 8b with control signals for controlling timing for detecting an electric charge, timing for generating an intensity signal and a spectral signal, and output timing thereof in the plurality of read circuits 8a and 8b. For example, the controller 3 provides a control signal so as to set electric charge detection timing in synchronization with external X-ray irradiation timing, and then provides a control signal so as to sequentially output an intensity signal and a spectral signal from each pixel 7d of the detection element board 7.

Figure 3:
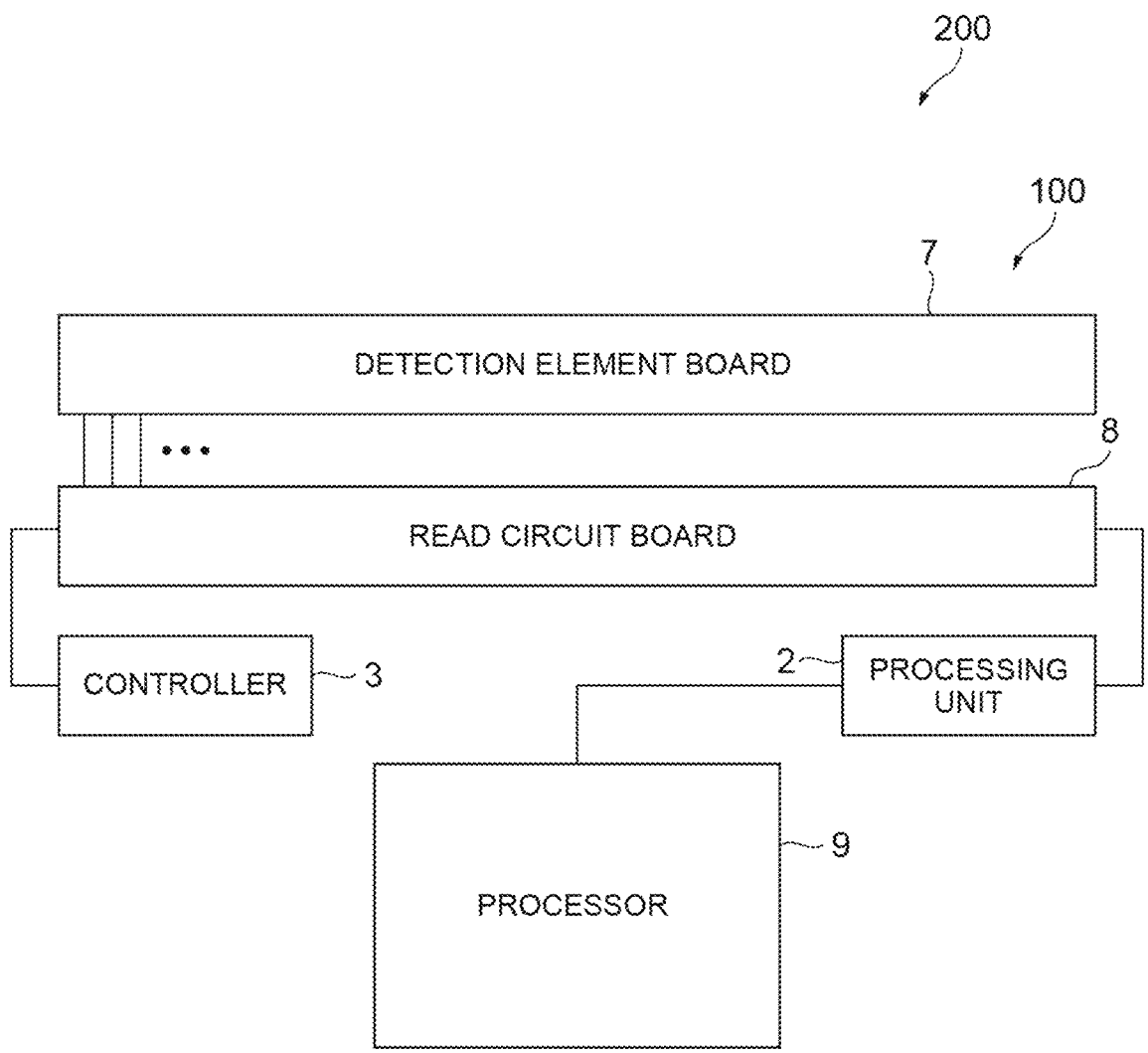
FIG. 3 is a block diagram illustrating a configuration of a radiation imaging device 200 according to the embodiment.

FIG. 3 is a block diagram illustrating a configuration of a radiation imaging device 200 according to the embodiment. The radiation imaging device 200 includes the above-mentioned radiation detector 100 and a processor 9. The processor 9 processes an intensity signal of each pixel and a spectral signal of each pixel output from the radiation detector 100 to generate and output a cross-sectional image of the subject. The processor 9 receives an intensity signal and a spectral signal from the processing unit 2 of the radiation detector 100 via a network by wired communication or wireless communication.

The processor 9 comprises a CPU (Central Processing Unit) that executes an operating system, an application program, etc., a main storage device including a ROM and a RAM, an auxiliary storage device including a hard disk, a flash memory, etc., a communication control device including a network card or a wireless communication module, an input device such as a keyboard, a mouse, or a touch panel, and an output device such as a monitor or a touch panel display. Each functional element of the processor 9 is realized by reading a predetermined program on the CPU or the main storage device and causing the CPU to execute the program. The CPU operates the communication control device, the input device, or the output device according to the program, and reads and writes data in the main storage device or the auxiliary storage device. Data or a database required for processing is stored in the main storage device or the auxiliary storage device.

Figure 4:
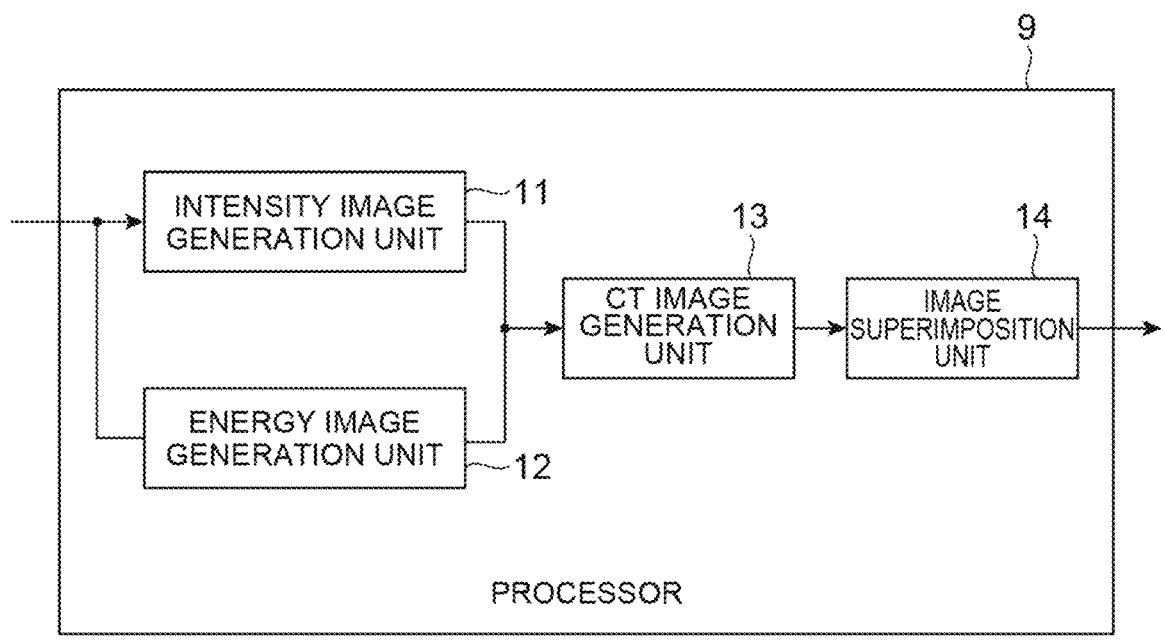
FIG. 4 is a block diagram illustrating an example of a functional configuration of a processor 9 of FIG. 3.

FIG. 4 is a block diagram illustrating an example of a functional configuration of the processor 9. The processor 9 includes an intensity image generation unit 11, an energy image generation unit 12, a CT image generation unit 13, and an image superimposition unit 14 as functional elements.

The intensity image generation unit 11 uses an intensity signal of each pixel and a spectral signal of each pixel output from the radiation detector 100 to generate a high-resolution intensity image showing an intensity distribution of an X-ray transmission image in the subject. That is, the intensity image generation unit 11 converts the intensity signal and the spectral signal of each image into a pixel value of each pixel of the intensity image. Here, upon acquiring only a spectral signal for a pixel corresponding to the read circuit 8a, the intensity image generation unit 11 integrates an intensity value for each piece of energy over all the energy based on the spectral signal, thereby performing conversion into an intensity value of the corresponding pixel.

The energy image generation unit 12 uses a spectral signal of each thinned-out pixel output from the radiation detector 100 to generate a low-resolution energy image showing an intensity distribution of an X-ray transmission image in a predetermined energy band in the subject for a plurality of energy bands. In the present embodiment, since the CT image generation unit 13 acquires two types of energy information by a dual energy CT (dual energy computed tomography: DECT) scheme, an energy image of two types of energy bands (for example, 25 keV and 65 keV energy bands) is generated. Here, the energy image generation unit 12 integrates an intensity value for each of the two energy bands based on a spectral signal of a pixel corresponding to the read circuit 8a, thereby performing conversion into an intensity value of a pixel of the energy image.

The CT image generation unit 13 acquires high-resolution intensity images generated by the intensity image generation unit 11 for various irradiation directions of X-rays with respect to the subject, and analyzes the intensity images in the various irradiation directions, thereby generating a CT image showing a high-resolution distribution of linear attenuation coefficients on a predetermined fault plane of the subject. At this time, the CT image generation unit 13 may adopt a two-dimensional Fourier transform method, a filtered back projection method, an iterative reconstruction method, etc. as an image reconstruction method used when the CT image is generated.

Further, the CT image generation unit 13 acquires low-resolution energy images of a plurality of types of energy bands generated by the energy image generation unit 12 for various irradiation directions, and analyzes the low-resolution energy images, thereby generating a low-resolution CT image of a plurality of types of energy bands on a predetermined tomographic plane of the subject. At this time, the CT image generation unit 13 may adopt the above-mentioned methods as an image reconstruction method used when the CT image is generated.

Further, the CT image generation unit 13 generates a physical property distribution image showing a distribution of physical properties on a fault plane of the subject based on low-resolution CT images of a plurality of types of energy bands. For example, when the dual energy CT scheme is adopted, the CT image generation unit 13 uses the following equation;

$$\mu=\rho[Z^4 F(E,Z)+G(E,Z)]$$

indicating a relationship among a linear attenuation coefficient $\mu$, an energy value E, an electron density $\rho$, an atomic number Z, a photoelectric absorption attenuation coefficient F, and a scattering attenuation coefficient G to calculate an effective atomic number Z and the electron density $\rho$ for each pixel based on the linear attenuation coefficient shown by a CT image of two energy bands. Here, the photoelectric absorption attenuation coefficient F and the scattering attenuation coefficient G are known functions (for example, mapping tables) with the energy value E and the atomic number Z as arguments, and are stored in the processor 9 in advance. Then, the CT image generation unit 13 assigns the calculated effective atomic number Z or electron density $\rho$ for each pixel, thereby generating a physical property distribution image showing a low-resolution distribution of the effective atomic number Z or electron density $\rho$.

The image superimposition unit 14 sets each pixel value of the high-resolution CT image generated by the CT image generation unit 13 as luminance information of an output image, sets each pixel value of the low-resolution physical property distribution image generated by the CT image generation unit 13 as color information of an output image, and combines the luminance information and the color information for each pixel, thereby generating an output image which is a color image. As a result, the image superimposition unit 14 may output a distribution of linear attenuation coefficients on a predetermined fault plane of the subject and a distribution of physical property values on the fault plane so that the distributions are simultaneously visually recognizable. In such an output image, by superimposing a low-resolution color grid (line or dot) on a high-resolution black-and-white image, a viewer may be allowed to recognize the image as a high-resolution color image by an optical illusion.

Figure 5:
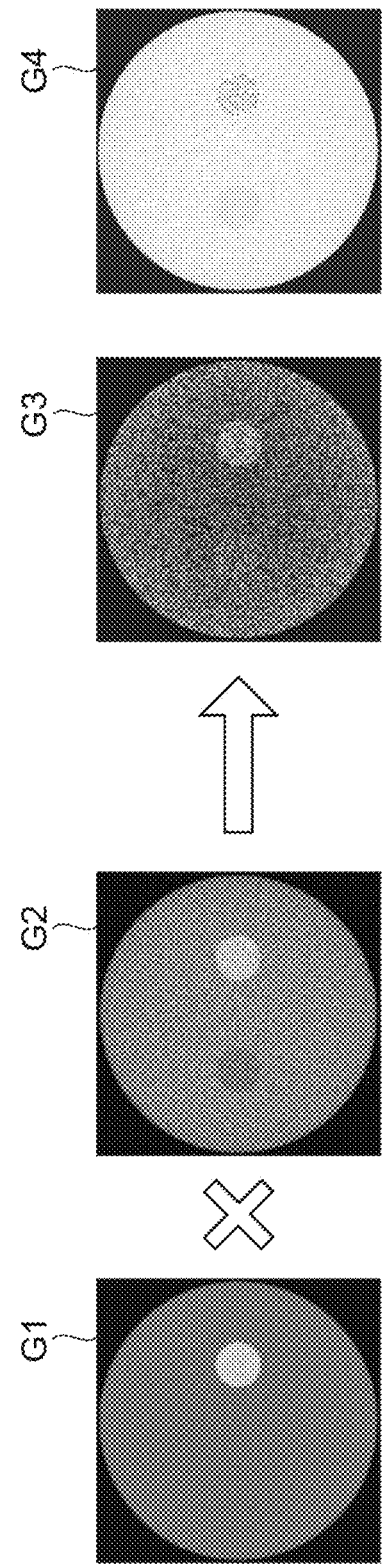
FIG. 5 is a diagram illustrating examples of an image processed by the processor 9.
Figure 6:
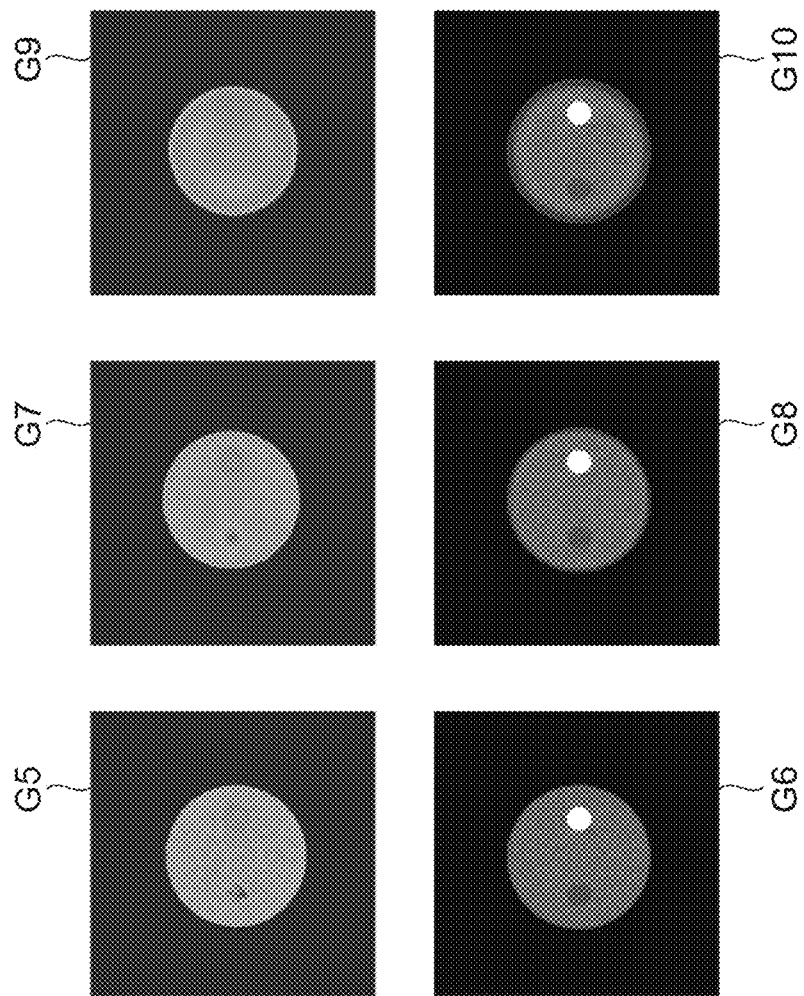
FIG. 6 is a diagram illustrating examples of an image processed by the processor 9.

FIGS. 5 and 6 illustrate examples of an image processed by the processor 9 with a model imitating a bone and a blood vessel as a subject. In FIG. 5, an image G1 shows a low-resolution CT image in an energy band of 25 keV, an image G2 shows a low-resolution CT image in an energy band of 65 keV, and an image G3 shows a physical property distribution image of an effective atomic number generated based on the image G1 and the image G2, and an image G4 shows a physical property distribution image of the electron density generated based on the image G1 and the image G2. In FIG. 6, an image G5 shows a physical property distribution image of the electron density when a spectral signal is thinned out every eight pixels, an image G6 shows an output image on which the image G5 is superimposed, an image G7 shows a physical property distribution image of the electron density when a spectral signal is thinned out every 16 pixels, an image G8 shows an output image on which the image G7 is superimposed, an image G9 shows a physical property distribution image of the electron density when a spectral signal is thinned out every 32 pixels, and an image G10 shows an output image on which the image G9 is superimposed. From these results, it may be seen that when the degree of thinning is every 8 or 16, the electron density distribution clearly appears in the output image, and the physical property distribution may be visually displayed.

In the radiation detector 100 described above, electric charges corresponding to energy of X-rays incident on a plurality of pixels 7d of the detection element board 7 are generated, and an intensity signal indicating an intensity distribution of transmitted X-rays based on the electric charges is output from each of the read circuits 8a and 8b corresponding to the respective pixels 7d. At the same time, in each of some read circuits 8a thinned out from the plurality of read circuits 8a and 8b, a spectral signal related to a spectrum of a transmitted X-ray based on electric charges is generated and output. In this way, it is possible to reduce energy information for each pixel 7d output by the radiation detector 100 while maintaining the resolution of the intensity information of the transmitted X-ray image of the subject, and as a result, it is possible to reduce processing load and power consumption while maintaining the resolution of the image of the subject to be output.

In the present embodiment, some read circuits 8a generate spectral signals based on electric charges generated in pixels 7d disposed corresponding to the read circuits 8a. In this case, a spectral signal related to a spectrum of a transmitted X-ray incident on each pixel 7d is generated and output based on electric charges generated in some pixels 7d thinned out from the plurality of pixels 7d. As a result, it is possible to output intensity information and energy information while reducing the processing load and power consumption.

In the present embodiment, some read circuits 8a generate, as spectral signals, data indicating a plurality of combinations of energy of a transmitted X-ray and an intensity value corresponding to the energy. According to this configuration, energy information for obtaining a distribution of physical property data may be efficiently output from only some thinned-out read circuits 8a. As a result, intensity information and energy information may be output while reducing the processing load and power consumption.

According to the radiation imaging device 200 according to the present embodiment, since the radiation detector 100 described above is provided, it is possible to realize image generation based on intensity information and energy information while reducing the processing load and power consumption.

In particular, the processor 9 provided in the radiation imaging device 200 generates information representing an X-ray transmission image of the subject as high-resolution luminance information based on intensity signals output from a plurality of read circuits 8a and 8b, generates information representing a distribution of physical properties of the subject as low-resolution color information based on spectral signals output from some read circuits 8a, and generates a color image of the subject by combining the luminance information and the color information. According to this configuration, a delicate CT image of the subject may be efficiently generated in a state where a physical property distribution may be visually recognized at the same time.

Further, in the present embodiment, the processor 9 may have a function of reconstructing a CT image based on an intensity signal and a spectral signal output from the radiation detector 100. In such a configuration, spectral CT having reduced processing load and power consumption may be realized.

The radiation detector of the disclosure is not limited to the above-described embodiment. The radiation detector of the disclosure may be variously modified without departing from the subject matter of the claims.

The number of pixels or the degree of thinning in the radiation detector 100 in the above-described embodiment is an example, and may be changed in various ways.

Further, the data output by the radiation detector 100 is not limited to the intensity signal and the spectral signal based on the electric charges corresponding to the energy of the radiation, and may be a signal based on electric charges corresponding to the number of radiation particles incident on each pixel of the radiation detector 100.

Figure 7:
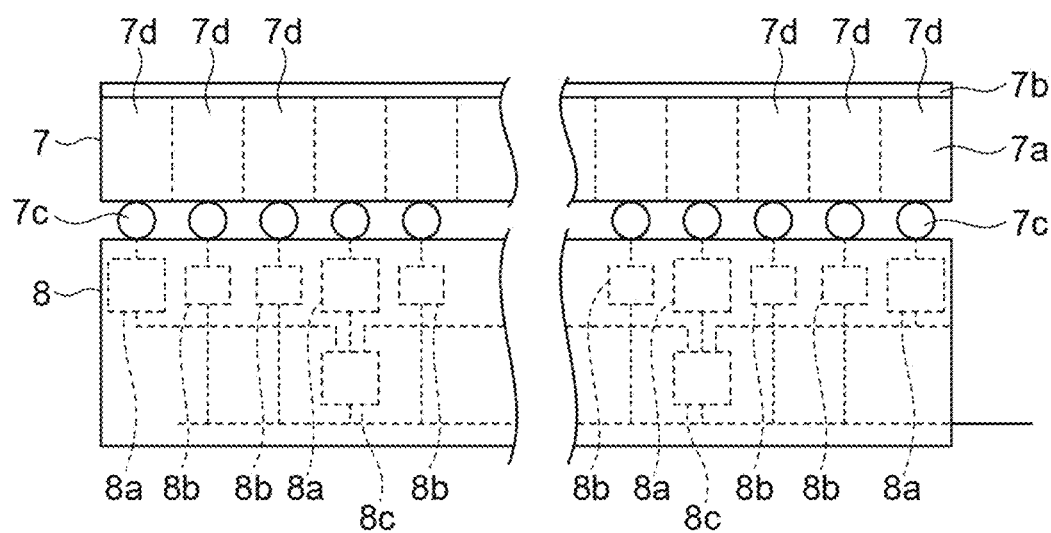
FIG. 7 is a cross-sectional view of a radiation detection element 1 in a modification.

The configuration of the read circuit board 8 of the radiation detector 100 in the above-described embodiment may be changed to a configuration illustrated in FIG. 7. In a modification illustrated in FIG. 7, a plurality of read circuits 8c connected to read circuits 8a within a predetermined range adjacent to each other in two-dimensional directions are further provided in the read circuit board 8. Each of the read circuits 8c generates and outputs one spectral signal by integrating a spectral signal based on an electric charge generated by a pixel 7d provided to face one read circuit 8a, and a spectral signal generated by one or more read circuits 8a facing a pixel 7d within a predetermined range of the pixel 7d (binning processing is performed). For example, upon integrating a plurality of spectral signals into one signal, the read circuit 8c performs integration by adding up or averaging intensity values for each of piece of energy.

According to this modification, based on electric charges generated in a plurality of pixels 7d included in a predetermined range among a plurality of pixels 7d, a spectral signal obtained by integrating spectra of transmitted X-rays incident on the respective pixels 7d in the predetermined range is generated and output. As a result, it is possible to output intensity information and energy information while reducing the processing load and power consumption.

Further, in the modification, all the read circuits facing the pixels 7d of the radiation detection element 1 may each have a function of generating a spectral signal, and a plurality of read circuits 8c may each perform binning process on spectral signals output from read circuits within a predetermined range.

REFERENCE SIGNS LIST

100: radiation detector, 200: radiation imaging device, 7: detection element board (electric charge generation unit), 7d: pixel (electric charge generation region), 8: read circuit board, 8a, 8b, 8c: read circuit, 9: processor.

The invention claimed is:

1. A radiation detector comprising:
   an electric charge generation unit including a plurality of electric charge generation regions each configured to generate an electric charge corresponding to energy or the number of particles of radiation penetrating a subject, the plurality of electric charge generation regions being two-dimensionally arranged; and
   a plurality of read circuits being stacked with the electric charge generation unit, the plurality of read circuits each configured to output an intensity signal of the radiation based on the electric charge generated by each of the plurality of electric charge generation regions,
   wherein some read circuits thinned out from the plurality of read circuits each generate a spectral signal related to a spectrum of the radiation based on the electric charge and output the spectral signal.

2. The radiation detector according to claim 1, wherein the some read circuits each generate the spectral signal based on the electric charge generated in each of the electric charge generation regions disposed to correspond to the read circuits.

3. The radiation detector according to claim 1, wherein the some read circuits each generate the spectral signal based on the electric charge generated in each of the corresponding electric charge generation regions disposed to correspond to the read circuits and the electric charge generated in the electric charge generation regions within a predetermined range of each of the corresponding electric charge generation regions.

4. The radiation detector according to claim 1, wherein the some read circuits each generate, as the spectral signal, data indicating a plurality of combinations of energy of the radiation and an intensity value corresponding to the energy.

5. A radiation imaging device comprising:
   the radiation detector according to claim 1; and
   a processor configured to generate an image based on the intensity signal and the spectral signal output from the radiation detector.

6. The radiation imaging device according to claim 5, wherein the processor generates information representing an image of the subject as high-resolution luminance information based on the intensity signal output from each of the plurality of read circuits, generates information representing a distribution of physical properties of the subject as low-resolution color information based on the spectral signal output from each of the some read circuits, and generates a color image of the subject by combining the luminance information and the color information.

7. The radiation imaging device according to claim 5, wherein the processor has a function of reconstructing a CT image based on the intensity signal and the spectral signal output from the radiation detector.

* * * * *